United States Patent
Li et al.

(10) Patent No.: US 9,101,773 B2
(45) Date of Patent: Aug. 11, 2015

(54) CROSS-CHANNEL NOISE DETECTOR IN IMPLANTABLE MEDICAL DEVICES

(75) Inventors: Dan Li, Shoreview, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1032 days.

(21) Appl. No.: 12/693,512

(22) Filed: Jan. 26, 2010

(65) Prior Publication Data

US 2010/0204745 A1 Aug. 12, 2010

Related U.S. Application Data

(60) Provisional application No. 61/150,682, filed on Feb. 6, 2009.

(51) Int. Cl.
*A61N 1/365* (2006.01)
*A61N 1/37* (2006.01)
*A61N 1/39* (2006.01)

(52) U.S. Cl.
CPC ............. *A61N 1/3704* (2013.01); *A61N 1/3718* (2013.01); *A61N 1/3925* (2013.01)

(58) Field of Classification Search
CPC .... A61B 5/0464; A61B 5/046; A61N 1/3627; A61N 1/3682; A61N 1/3706; A61N 1/37
USPC ....................................... 600/518; 607/25, 27
See application file for complete search history.

(56) References Cited

U.S. PATENT DOCUMENTS

| 5,348,021 A | 9/1994 | Adams et al. |
| 5,496,350 A | 3/1996 | Lu |
| 5,558,098 A | 9/1996 | Fain |
| 5,697,958 A | 12/1997 | Paul et al. |

(Continued)

FOREIGN PATENT DOCUMENTS

| CN | 1829554 A | 9/2006 |
| CN | 102307619 B | 8/2014 |

(Continued)

OTHER PUBLICATIONS

Swerdlow, C. D., et al., "Implantable Cardioverter Defibrillator Shocks: A Troubleshooting Guide", *Reviews in Cardiovascular Medicine*, 2(2), (2001), 61-72.

(Continued)

*Primary Examiner* — Christopher D Koharski
*Assistant Examiner* — Michael Carey
(74) *Attorney, Agent, or Firm* — Schwegman Lundberg & Woessner, P.A.

(57) ABSTRACT

An apparatus comprises a primary cardiac signal sensing circuit to sense a first cardiac signal, a secondary cardiac signal sensing to sense a second cardiac signal, and an arrhythmia detection circuit. The primary sensing circuit includes at least first and second implantable electrodes, and the secondary sensing circuit includes a third implantable electrode to deliver high-energy shock therapy. The arrhythmia detection circuit detects tachyarrhythmia using the primary sensing circuit, determines correspondence between events sensed with the primary sensing circuit and events sensed with the secondary sensing circuit, and deems whether a detected rhythm is indicative of noise or is indicative of an arrhythmia according to the determined correspondence.

20 Claims, 6 Drawing Sheets

(56) References Cited

U.S. PATENT DOCUMENTS

| | | | |
|---|---|---|---|
| 5,702,425 | A | 12/1997 | Wickham |
| 5,755,738 | A | 5/1998 | Kim et al. |
| 5,861,008 | A | 1/1999 | Obel et al. |
| 6,230,059 | B1 | 5/2001 | Duffin |
| 6,321,115 | B1 | 11/2001 | Mouchawar et al. |
| 6,505,071 | B1 | 1/2003 | Zhu et al. |
| 6,522,925 | B1 | 2/2003 | Gilkerson et al. |
| 6,745,076 | B2 | 6/2004 | Wohlgemuth et al. |
| 6,760,615 | B2 * | 7/2004 | Ferek-Petric ............ 600/518 |
| 6,862,476 | B2 | 3/2005 | Mouchawar et al. |
| 7,027,858 | B2 | 4/2006 | Cao et al. |
| 7,062,328 | B1 | 6/2006 | Levine et al. |
| 7,155,275 | B2 * | 12/2006 | Linder et al. ............ 600/509 |
| 7,215,993 | B2 | 5/2007 | Lin |
| 7,515,955 | B2 | 4/2009 | Linder et al. |
| 2006/0253162 | A1 | 11/2006 | Zhang et al. |
| 2006/0253164 | A1 | 11/2006 | Zhang et al. |
| 2007/0038253 | A1 * | 2/2007 | Kim et al. .................... 607/4 |
| 2007/0135856 | A1 | 6/2007 | Knudson et al. |
| 2007/0239051 | A1 | 10/2007 | Ghanem et al. |
| 2008/0082012 | A1 | 4/2008 | Gunderson et al. |
| 2008/0161870 | A1 | 7/2008 | Gunderson |
| 2008/0228093 | A1 | 9/2008 | Dong et al. |

FOREIGN PATENT DOCUMENTS

| | | | |
|---|---|---|---|
| JP | 639041 | A | 2/1994 |
| JP | 2012517285 | A | 8/2012 |

OTHER PUBLICATIONS

"International Application Serial No. PCT/US2010/022028, Invitation to Pay Additional Fees and Partial Search Report mailed Apr. 27, 2010", 8 pgs.

"Australian Application Serial No. 2010210840, Examiner Report mailed Jun. 18, 2012", 4 pgs.

"Australian Application Serial No. 2010210840, Response filed Dec. 20, 2012 to Office Action mailed Jun. 18, 2012", 5 pgs.

"Japanese Application Serial No. 2011-549178, Decision of Rejection mailed Jun. 18, 2013", 6 pgs.

"Japanese Application Serial No. 2011-549178, Office Action mailed Jan. 29, 2013", With English Translation, 7 pgs.

"Japanese Application Serial No. 2011-549178, Response filed Mar. 29, 2013 to non-final office action dated Jan. 29, 2013", With English Claims, 15.

"Chinese Application Serial No. 201080006729.X, Office Action mailed Mar. 6, 2014", 5 pgs.

"Chinese Application Serial No. 201080006729.X, Office Action mailed Jun. 6, 2013", 7 pgs.

"Chinese Application Serial No. 201080006729.X, Office Action mailed Nov. 22, 2013", 9 pgs.

"Chinese Application Serial No. 201080006729.X, Response filed Jan. 22, 2014 to Office Action mailed Nov. 22, 2013", 14 pgs.

"Chinese Application Serial No. 201080006729.X, Response filed Aug. 20, 2013 to Office Action mailed Jun. 6, 2013", 10 pgs.

"European Application Serial No. 10701788.1, Examination Notification Art. 94(3) mailed Feb. 17, 2014", 4 pgs.

* cited by examiner

CROSS-CHANNEL NOISE DETECTOR IN IMPLANTABLE MEDICAL DEVICES

CROSS-REFERENCE TO RELATED APPLICATIONS

This application claims the benefit of U.S. Provisional Application No. 61/150,682, filed on Feb. 6, 2009, under 35 U.S.C. §119(e), which is hereby incorporated by reference.

BACKGROUND

Implantable medical devices (IMDs) are devices designed to be implanted into a patient. Some examples of these devices include cardiac function management (CFM) devices. CFMs include implantable pacemakers, implantable cardioverter defibrillators (ICDs), and devices that include a combination of pacing and defibrillation including cardiac resynchronization therapy. The devices are typically used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. In CFM devices, these events include heart chamber expansions or contractions. By monitoring cardiac signals indicative of expansions or contractions, IMDs are able to detect abnormally slow heart rate, or bradycardia. The IMDs are also able to detect abnormally rapid heart rate, or tachyarrhythmia. Some tachyarrhythmia is treated by delivering high-energy electrical shock therapy with the IMD. Patients that use IMDs may be adversely affected by noise sensed by the IMD sensing circuits. If an IMD incorrectly interprets noise, the IMDs may inappropriately deliver shock therapy, causing patient discomfort.

OVERVIEW

This document relates generally to systems, devices, and methods for monitoring cardiac electrophysiological parameters of a patient or subject. In example 1, an apparatus includes a primary cardiac signal sensing circuit configured to sense at least a first cardiac signal, at least one secondary cardiac signal sensing circuit configured to sense at least a second cardiac signal, and an arrhythmia detection circuit communicatively coupled to the primary and secondary cardiac signal sensing circuits. The primary cardiac signal sensing circuit includes or is configured to be coupled to at least first and second implantable electrodes and the secondary cardiac signal sensing circuit includes or is configured to be couple to at least a third implantable electrode that is different from the first and second electrode and is configured to deliver high-energy shock therapy. The arrhythmia detection circuit is configured to detect tachyarrhythmia using the primary sensing circuit, determine correspondence between events sensed with the primary sensing circuit and events sensed with the secondary sensing circuit, and deem whether a detected rhythm is indicative of noise or is indicative of an arrhythmia according to the determined correspondence.

In example 2, the arrhythmia detection circuit of example 1 is optionally configured to calculate variability of a delay between an event sensed with the primary sensing circuit and an event sensed with the secondary sensing circuit, and deem that the detected rhythm is indicative of noise when the calculated delay variability exceeds a threshold variability value.

In example 3, the arrhythmia detection circuit of any one or more of examples 1 and 2 is optionally configured to calculate a moving average of the variability, and deem that the detected rhythm is indicative of noise when the calculated moving average of the variability exceeds the threshold variability value.

In example 4, the arrhythmia detection circuit of any one or more of examples 1-3 is optionally configured to determine a number of events sensed with the primary sensing circuit and a number of events sensed with the secondary sensing circuit, and deem that the detected rhythm is indicative of noise when the number of events sensed with the primary sensing circuit during a period of time exceeds the number of events sensed with the secondary sensing circuit during the same time period by a threshold value.

In example 5, the arrhythmia detection circuit of example 4 is optionally configured to calculate a ratio of the number of events sensed with the primary sensing circuit to the number of events sensed with the secondary sensing circuit during the time period, and deem that the detected rhythm is indicative of noise when the calculated ratio exceeds a threshold ratio value.

In example 6, the arrhythmia detection circuit of any one or more of examples 1-5 is optionally configured to determine a measure of complexity of a morphology of the first cardiac signal and a measure of complexity of a morphology of the second cardiac signal, and deem that the detected rhythm is indicative of noise when the measure of complexity of the first cardiac signal differs from the measure of complexity of the second cardiac signal by more than a threshold value.

In example 7, the arrhythmia detection circuit of any one or more of examples 1-6 is optionally configured to calculate a measure of similarity between the first and second cardiac signals and deem that the detected rhythm is indicative of an arrhythmia when the measure of similarity satisfies a similarity measure threshold value. The measure of similarity includes at least one of a cross-covariance of the first and second cardiac signals, a cross-correlation of the first and second cardiac signals, and a coherence of the first and second cardiac signals.

In example 8, the arrhythmia detection circuit of any one or more of examples 1-7 is optionally configured to calculate a cross entropy between the first and second cardiac signals, and deem that the detected rhythm is indicative of an arrhythmia when the calculated cross-entropy satisfies a threshold cross-entropy value.

In example 9, the apparatus of any one or more of examples 1-8 optionally includes a switching circuit communicatively coupled to the primary sensing circuit, secondary sensing circuit, and the arrhythmia detection circuit. The switching circuit is configured to switch at least one of a first filter circuit included in the primary sensing circuit to the secondary sensing circuit and a second filter circuit included in the secondary sensing circuit to the primary sensing circuit. The arrhythmia detection circuit is optionally configured to, when detecting the rhythm, determine a rate of events sensed with at least one of the primary sensing circuit and the secondary sensing circuit, switch at least one of the first filter circuit included with the primary sensing circuit to the secondary sensing circuit, and the second filter circuit included with the secondary sensing circuit to the primary sensing circuit, determine a rate of events sensed with the sensing circuit when the filter circuit is switched, and deem that the detected rhythm is indicative of noise when the determined rate of depolarization events changes by more than a threshold rate value after the filter circuit is switched.

In example 10, the apparatus of any one or more of examples 1-8 optionally includes a switching circuit communicatively coupled to the primary sensing circuit, secondary sensing circuit, and the arrhythmia detection circuit. The switching circuit is configured to switch at least one of the electrodes of the primary sensing circuit to the secondary sensing circuit and the electrodes of the secondary sensing circuit to the primary sensing circuit. The arrhythmia detection circuit is optionally configured to, when detecting the rhythm, determine a rate of events sensed with at least one of the primary sensing circuit and the secondary sensing circuit, switch the electrodes of at least one of the primary sensing circuit to the secondary sensing circuit and the secondary sensing circuit to the primary sensing circuit, determine a rate of events sensed with the sensing circuit when the electrodes are switched, and deem that the detected rhythm is indicative of noise when the determined rate of events changes by more than a threshold rate value after the electrodes are switched.

In example 11, the apparatus of any one or more of examples 1-10 optionally includes a therapy circuit communicatively coupled to the electrodes of the primary and secondary sensing circuits, and a tachyarrhythmia detection circuit communicatively coupled to the primary and secondary sensing circuits. The tachyarrhythmia detection circuit is configured to determine whether a detected rhythm, deemed to be an arrhythmia instead of noise, is a valid tachyarrhythmia, and to initiate delivery of a therapy to the heart using the therapy circuit when the tachyarrhythmia is determined to be valid.

In example 12, a method includes sensing a first cardiac signal using a primary sensing circuit that includes or is configured to be coupled to a first and a second implantable electrode, sensing a second cardiac signal using at least one secondary sensing circuit, that includes or is configured to be coupled to at least a third implantable electrode that is different from the first and second electrodes and is configured to deliver high-energy shock therapy, detecting tachyarrhythmia using the primary sensing circuit, determining correspondence between events in the first cardiac signal sensed with the primary sensing circuit and events in the second cardiac signal sensed with the secondary sensing circuit, and deeming whether the detected rhythm is indicative of noise or is indicative of an arrhythmia according to the determined correspondence.

In example 13, the determining correspondence between events of example 12 optionally includes calculating variability of a delay between an event sensed with the primary sensing circuit and an event sensed with the secondary sensing circuit, and the deeming whether the detected rhythm is indicative of noise or of an arrhythmia includes deeming that depolarization events sensed with the primary sensing circuit are indicative of noise when the calculated delay variability exceeds a threshold variability value.

In example 14, the calculating variability of the delay of example 13 optionally includes calculating a moving average of the variability, and the deeming whether the detected rhythm is indicative of noise includes deeming that events sensed with the primary sensing circuit are indicative of noise when the calculated delay variability average exceeds the threshold variability value.

In example 15, the determining correspondence between events of any one or more of examples 12-14 optionally includes determining a number of events sensed with the primary sensing circuit during a period of time and a number of events sensed with the secondary sensing circuit during the same time period, and the deeming whether the detected rhythm is indicative of noise or of an arrhythmia includes deeming that the detected rhythm is indicative of noise when the number of events sensed during the time period with the primary sensing circuit exceeds the number of events sensed with the secondary sensing circuit during the time period by a threshold value.

In example 16, the method of example 15 optionally includes calculating a ratio of the number of events sensed with the primary sensing circuit during the time period to the number of events sensed with the secondary sensing circuit during the time period, and the deeming whether the detected rhythm is indicative of noise or an arrhythmia includes deeming that the detected rhythm is indicative of noise when the ratio exceeds a threshold ratio value.

In example 17, the determining correspondence between events sensed in the primary sensing circuit and events sensed in the secondary sensing circuit of any one or more of examples 12-16 optionally includes determining a measure of complexity of a morphology of the first cardiac signal and a measure of complexity of a morphology of the second cardiac signal, and the deeming whether the detected rhythm is indicative of noise or an arrhythmia includes deeming that the detected rhythm is indicative of noise when the measure of complexity of the first cardiac signal differs from the measure of complexity of the second cardiac signal by more than a threshold value.

In example 18, the determining a measure of complexity of a morphology of cardiac signal of example 17 optionally includes determining a cross entropy between the first and second cardiac signals.

In example 19, the determining correspondence between events sensed with the primary sensing circuit and events sensed with the secondary sensing circuit of any one or more of examples 12-18 optionally includes determining a measure of similarity between the first and second cardiac signals and the deeming whether the detected rhythm is indicative of noise or an arrhythmia includes deeming that the detected rhythm is indicative of arrhythmia when the measure of similarity satisfies a similarity measure threshold value. The measure of similarity includes at least one of a cross-covariance of the first and second cardiac signals, a cross-correlation of the first and second cardiac signals, and a coherence of the first and second cardiac signals.

In example 20, the determining correspondence between events sensed with the primary sensing circuit and events sensed with the secondary sensing circuit of any one or more of examples 12-19 optionally includes determining a rate of events with at least one of the primary sensing circuit and the secondary sensing circuit, switching at least one of a first filter circuit included with the primary sensing circuit to the secondary sensing circuit, and a second filter circuit included with the secondary sensing circuit to the primary sensing circuit, and determining a rate of events sensed with the sensing circuit when the filter circuit is switched, and the deeming whether the detected rhythm is indicative of noise or an arrhythmia includes deeming that the detected rhythm is indicative of noise when the determined rate of events changes by more than a threshold rate value after the filter circuit is switched.

In example 21, the determining correspondence between events sensed with the primary sensing circuit and events sensed with the secondary sensing circuit of any one or more of examples 12-20 optionally includes determining a rate of events sensed with at least one of the primary sensing circuit and the secondary sensing circuit, switching the electrodes of at least one of the primary sensing circuit to the secondary sensing circuit and the secondary sensing circuit to the primary sensing circuit, and determining a rate of events sensed with the sensing circuit when the electrodes are switched, and the deeming whether the detected rhythm is indicative of noise or an arrhythmia includes deeming that the detected rhythm is indicative of noise when the determined rate of events changes by more than a threshold rate value after the electrodes are switched.

In example 22, the method of any one or more of examples 12-21 optionally includes determining whether the detected rhythm is a valid tachyarrhythmia when the detected rhythm is deemed to be an arrhythmia, and delivering at least one of anti-tachycardia pacing and high-energy shock therapy using at least one implantable electrode when the detected rhythm is deemed to be a valid tachyarrhythmia.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

The present application discusses, among other things, systems and methods for detecting ventricular tachyarrhythmia. When a tachyarrhythmia such as ventricular tachycardia (VT) is detected, IMDs are designed to provide therapy to the patient. ICDs treat VT by delivering a high-energy electrical shock to the heart. Other IMDs provide anti-tachycardia pacing (ATP). ATP uses lower energy pacing energy to establish a regular rhythm in a heart. This allows the tachycardia to be converted to a normal heart rhythm without exposing the patient to high-energy defibrillation therapy that can be painful to the patient.

Some IMDs are able to provide both ATP and defibrillation. When tachycardia is detected, the device may try to convert the arrhythmia with ATP before resorting to high-energy defibrillation. The type of tachyarrhythmia detected may determine what type of therapy the device uses in trying to convert the arrhythmia.

Figure 1:
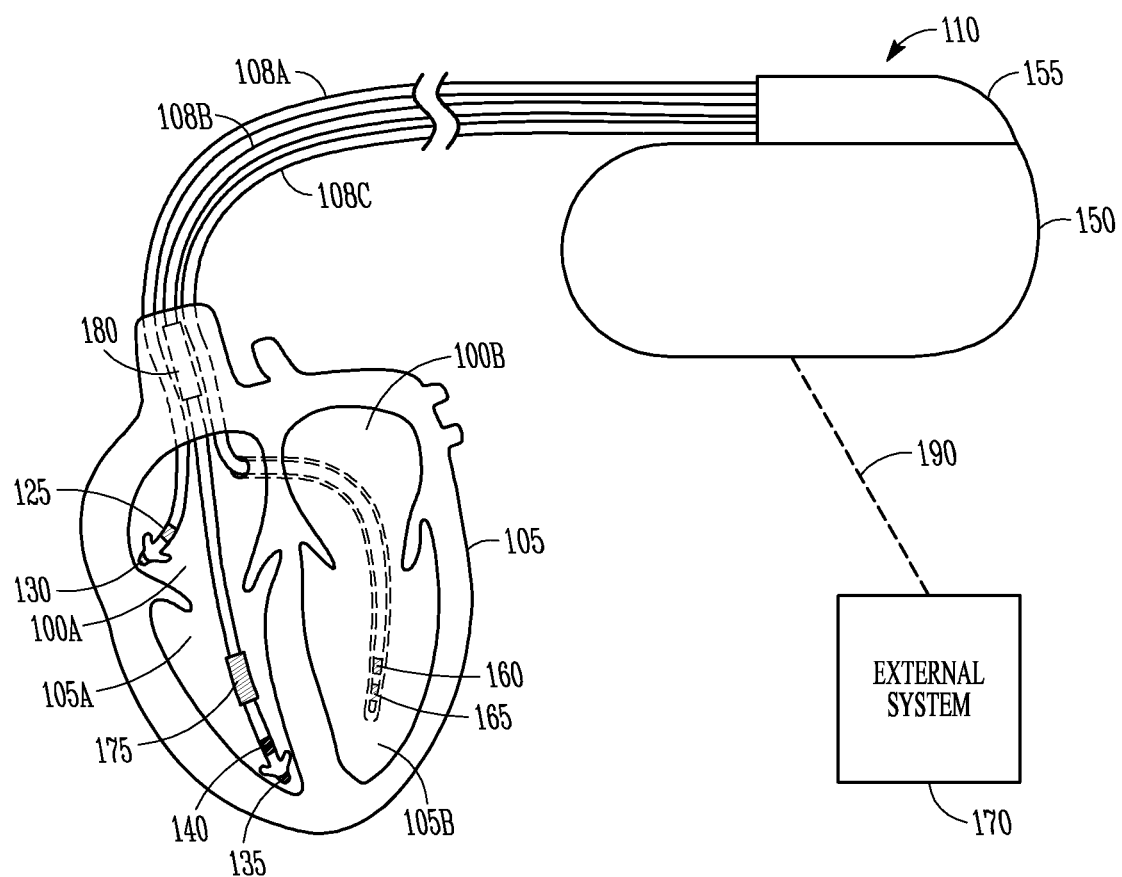
FIG. 1 is an illustration of portions of a system that uses an IMD.
Figure 2A:
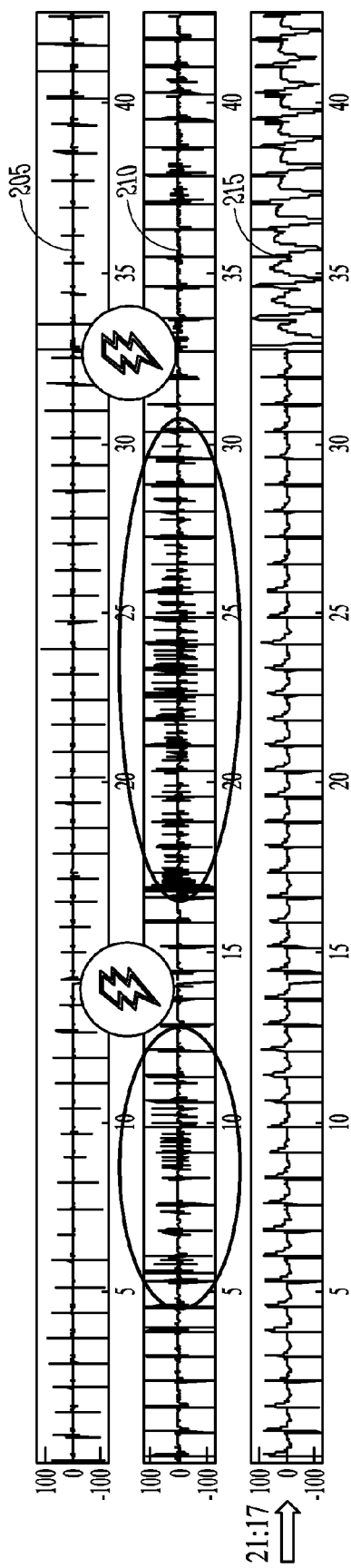
FIGS. 2A through 2D show several internal electrogram signals that include episodes of incorrect identification of diaphragmatic myopotentials.
Figure 2B:
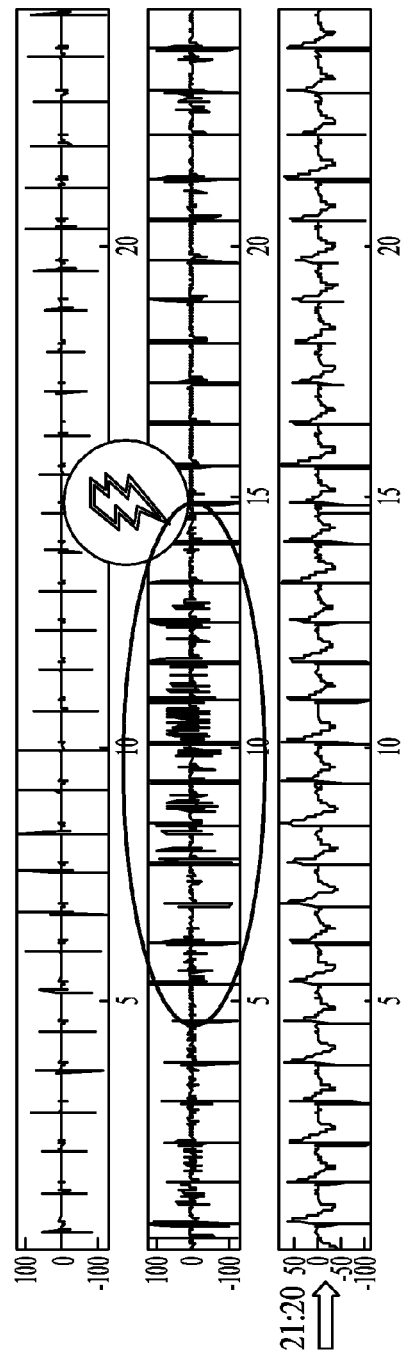
Figure 2C:
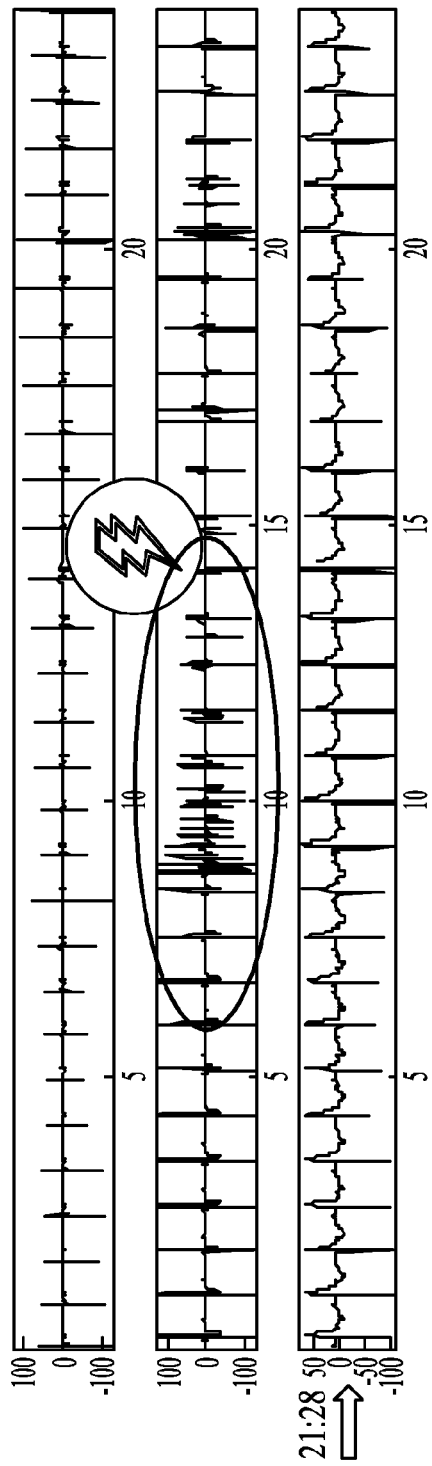
Figure 2D:
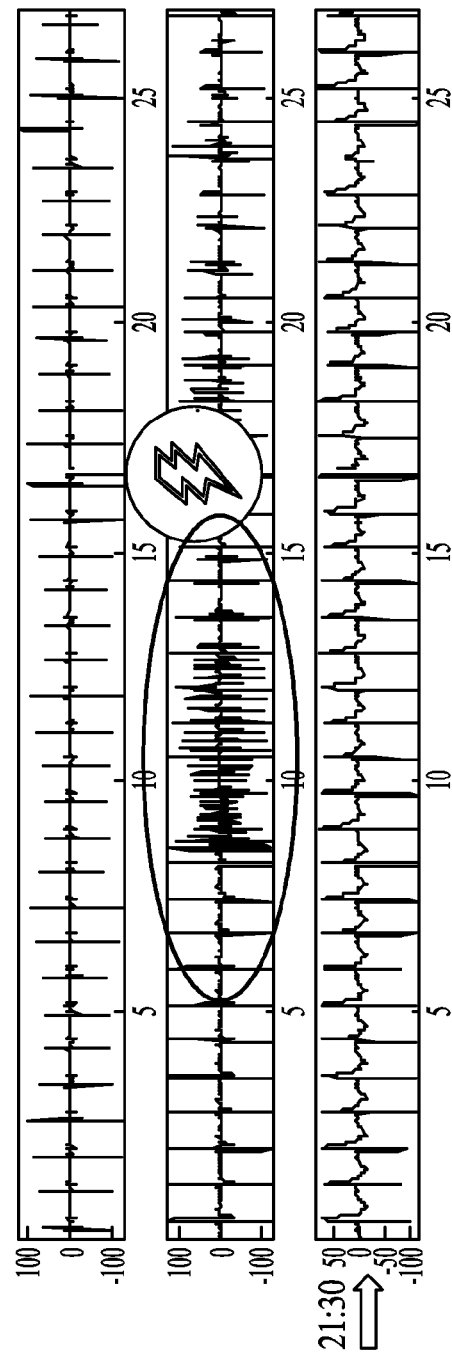

FIG. 1 is an illustration of portions of a system that uses an IMD 110. Examples of IMD 110 include, without limitation, a pacer, a defibrillator, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Atrial lead 108A includes electrodes (electrical contacts, such as ring electrode 125 and tip electrode 130) disposed in an atrium 100A of heart 105 for sensing signals, or delivering pacing therapy, or both, to the atrium 100A.

Ventricular lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105.

The IMD 110 may include a third cardiac lead 108C attached to the IMD 110 through the header 155. The third cardiac lead 108C includes ring electrodes 160 and 165 placed in a coronary vein lying epicardially on the left ventricle (LV) 105B via the coronary vein 120.

Lead 108B may include a first defibrillation coil electrode 175 located proximal to tip and ring electrodes 135, 140 for placement in a right ventricle (RV), and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD can 150. This improves defibrillation by delivering current from the RV coil 175 more uniformly over the ventricular myocardium. In some examples, the therapy is delivered from the RV coil 175 only to the electrode formed on the IMD can 150.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrical contacts or "electrodes." Sensing among different sets of electrodes often provides directional information regarding the propagation of cardiac signals and is often referred to as sensing among different vectors. For example, in a single chamber ICD, sensing from a right ventricular tip electrode 135 to a right ventricular ring electrode 140 would be a first vector, and sensing from an RV coil 175 to an electrode on the can 150, or a header 155, would be second vector.

The sensing of signals by the IMD 110 may be susceptible to noise. The signal noise may be physiologic or non-physiologic in nature. Non-physiologic signal noise may be intracardiac in origin due to a separate electronic device providing electrical therapy. The IMD 110 may sense the therapy. Intracardiac non-physiologic signal noise may also be due to the sensing electrode or lead making electrical contact with an abandoned lead fragment.

Non-physiological noise can also be extracardiac (external to the heart) in origin. The noise may be due to the device itself, such as due to fracture of an IMD lead, a faulty set screw or adapter used for securing an IMD lead, or electronic "chatter" picked up by the IMD lead. Non-physiologic noise sources separate from the IMD include electrocautery during surgery, magnetic resonance imaging, a lithotripsy procedure, or transmissions from electronic surveillance equipment.

Physiologic noise can also be intracardiac or extracardiac in origin. Examples of intracardiac physiologic noise includes a low amplitude R-wave or a prolonged Q-T segment of a sensed cardiac activation signal that complicates identification of a T-wave, and dislodgement of a ventricular lead that complicates the sensing and identifying of a P-wave or causes double-counting of an R-wave.

Extracardiac physiologic noise includes over-sensing of abdominal or diaphragmatic myopotentials (DMPs). DMPs are electrical activation signals related to contractions of the diaphragm. DMPs may be sensed by the IMD due to the position of implanted leads used to sense cardiac myopotentials or due to failure of the insulation of the implanted leads. In the absence of a lead abnormality, over-sensing of noise that leads to inappropriate delivery of cardioverting or defibrillating shock therapy is most commonly due to DMPs. The DMPs are incorrectly identified by an IMD as ventricular tachyarrhythmia, such as ventricular fibrillation (VF) or VT for example. Consequently, accurately discriminating DMPs from actual arrhythmias reduces delivery of inappropriate shocks from devices with cardioverter/defibrillator capability.

FIGS. 2A through 2D show several internal electrogram signals (e-grams) that include five time-stamped episodes of incorrect identification of DMPs. The e-grams include three recorded signals. The three recorded signals begin in FIG. 2A and continue through FIG. 2B, FIG. 2C, and then FIG. 2D. The top signal 205 is an atrial e-gram sensed with electrodes implanted in or near an atrium; sometimes called an atrial channel. For example, in FIG. 1 an atrial sense channel or atrial vector may include tip electrode 130 and ring electrode 125. The middle signal 210 in FIGS. 2A through 2D is a ventricular e-gram recorded with electrodes implanted in or near a ventricle; sometimes called a ventricular channel. For example, in FIG. 1 a ventricular channel or vector may include tip electrode 135 and ring electrode 140 for the RV or ring electrodes 160 and 165 for the LV. The atrial channel or the ventricular channel is also sometimes referred to as a rate channel because they can be used to sense the heart's depolarization rate. The bottom signal 215 in FIGS. 2A through 2D is an e-gram sensed with electrodes that are also used to deliver the high-energy shock therapy; sometimes called a shock channel or shock vector. For example, in FIG. 1 a shock channel may include defibrillation coil electrode 175 and can electrode 150.

The circled sections of the ventricular e-grams indicate episodes of sensed DMPs that resulted in an IMD delivering an inappropriate shock to the patient or subject. The time stamps on the left show that incorrectly identifying DMPs as tachyarrhythmia may involve multiple consecutive episodes of incorrect detection and inappropriate deliveries of shock therapy.

The shock channel does not sense the DMPs evident in the ventricular channel, or rate channel. One reason for the difference in sensing is the difference in electrode configuration between the two sensing channels. A lead or electrode of the ventricular channel (e.g., tip electrode 135) may be in a position proximal to the diaphragm, while the leads and electrodes of the shock channel typically are not in such a position. Another reason is the shock channel may use different filtering in sensing a cardiac signal. The shock channel may have a lower filter pass-band than the ventricular channel (e.g., 2.2 Hz-80.3 Hz for the shock channel and 20.8 Hz-171 Hz for the ventricular channel). This filtering results in the higher frequencies associated with DMPs being attenuated by the shock channel filtering.

Figure 3A:
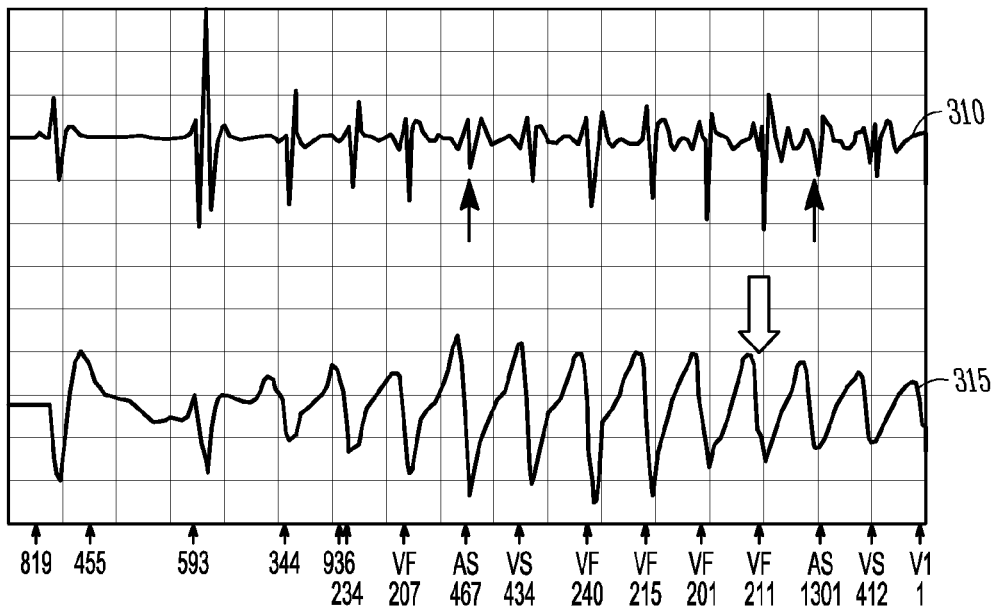
FIGS. 3A through 3C shows internal electrogram signals that include episodes of tachyarrhythmia.
Figure 3B:
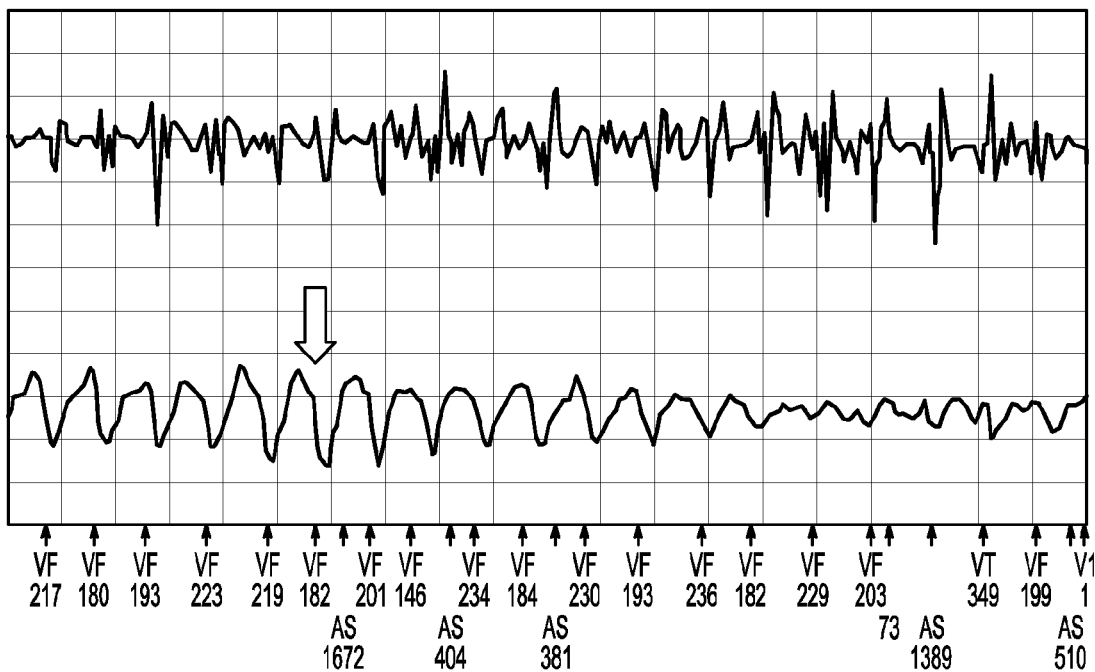
Figure 3C:
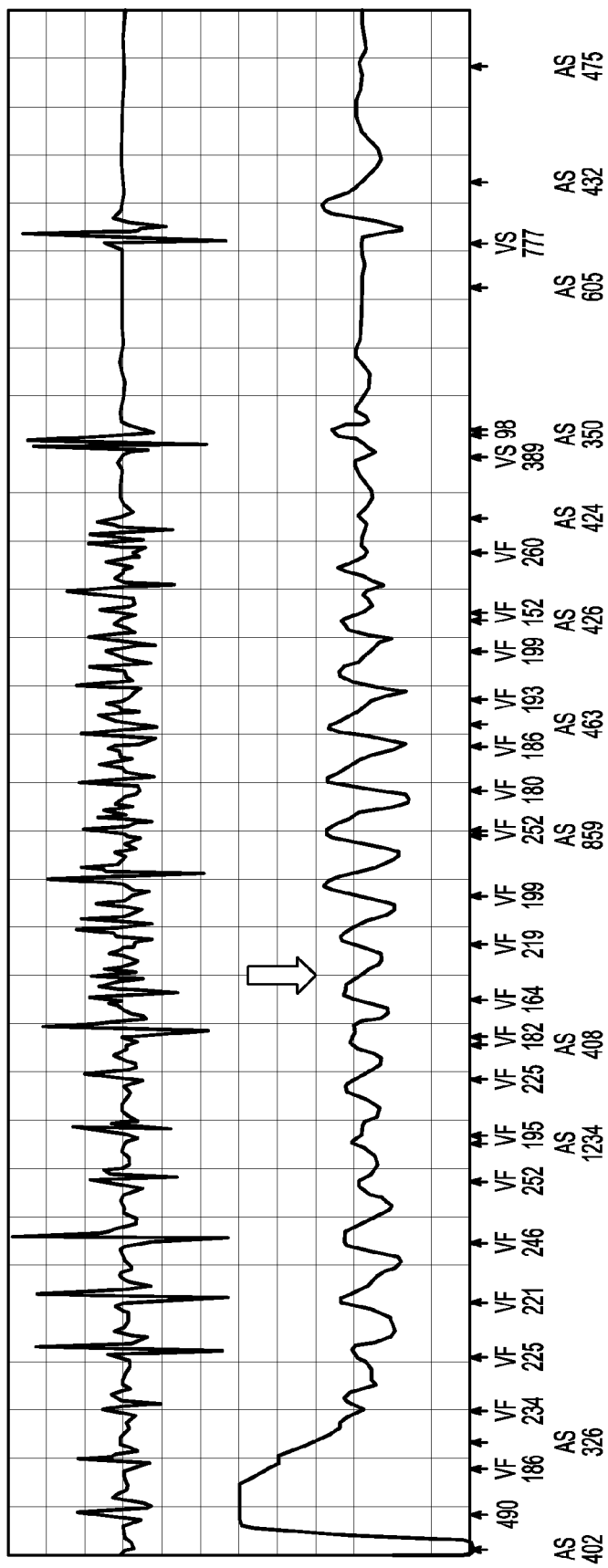

FIGS. 3A through 3C show internal e-gram signals that include episodes of tachyarrhythmia (VF). The e-gram signals begin in FIG. 3A and then continue through FIGS. 3B and 3C. The top trace 310 in the Figures is a ventricular e-gram sensed with a ventricular channel and the bottom trace 315 in the Figures is an e-gram sensed with the shock channel. Note that there is correspondence between the activity sensed with the ventricular channel and the activity sensed with the shock channel. During the episodes of VF shown in the Figures (indicated by the "VF" markers at the bottom of the graphs), the signals sensed by the ventricular channel covariate with the signals sensed by the shock channel. Monitoring correspondence between one or more rate channels and the shock channel may lead to an IMD more accurately discriminating noise from tachyarrhythmia.

Figure 4:
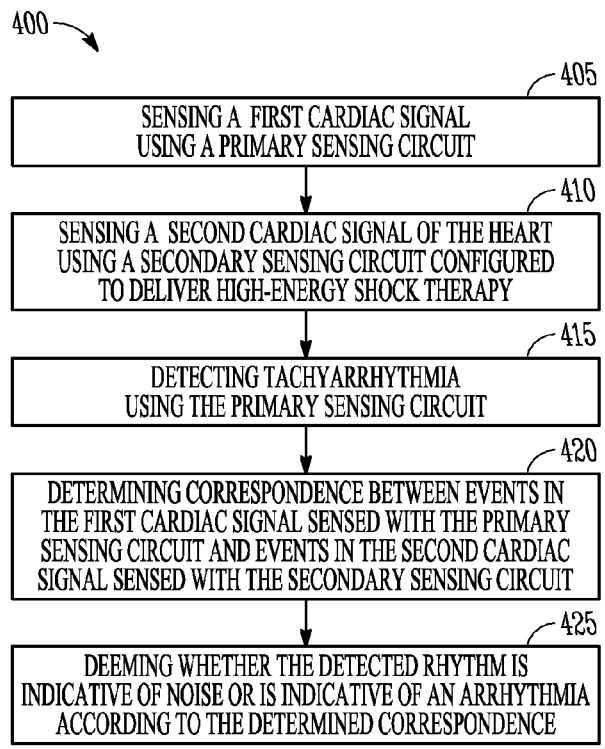
FIG. 4 is a diagram of an example of a method of identifying noise in a signal sensed by an IMD.

FIG. 4 is a diagram of an example of a method 400 of identifying noise in a signal sensed by an IMD. At block 405, a first cardiac signal is sensed using a primary sensing circuit. In some examples, the primary sensing circuit is a rate channel and includes a first and a second implantable electrode, such as a ventricular rate channel electrode pair as discussed previously.

At block 410, a second cardiac signal of the heart is sensed using at least one secondary sensing circuit. In some examples, the secondary sensing circuit is a shock channel and includes a third implantable electrode that is different from the first and second electrodes of the primary channel. The third implantable electrode is configured to deliver high-energy shock therapy, such as RV coil electrode 175 in FIG. 1. At least two electrodes are used in the secondary sensing circuit. The other electrode may be a rate channel electrode such as ring electrode 140, or may be another shock channel electrode such as the can electrode 150. In certain examples, the third electrode is a combination electrode, such as the electrode formed by electrically connecting the RV coil electrode 175 and the SVC coil electrode 180.

At block 415, tachyarrhythmia is detected using the primary sensing circuit. For example, the primary sensing circuit may detect a rate that exceeds a tachyarrhythmia rate zone threshold, or may detect a specified number of fast beasts occurring within a specified time period.

At block 420, correspondence is determined between events in the first cardiac signal sensed with the primary sensing circuit and events in the second cardiac signal sensed with the secondary sensing circuit. In some examples, the events are initially detected as being heart depolarizations.

At block 425, whether the detected rhythm is indicative of noise or is indicative of an arrhythmia is deemed or declared according to the determined correspondence. Therefore, it can be seen that the method 400 uses a cascaded noise detection technique. First, the arrhythmia is detected with a primary sensing channel. Second, association between the primary sensing channel and a secondary sensing is used to determine whether the detected event is indeed an arrhythmia or is noise.

Figure 5:
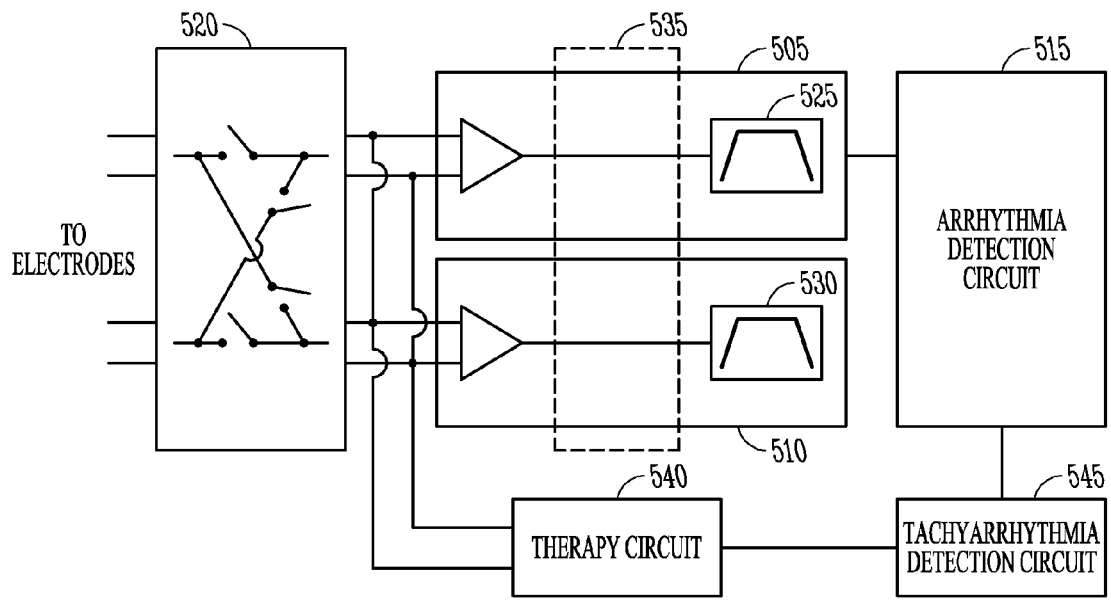
FIG. 5 shows a block diagram of an embodiment of a device to detect cardiac events.

FIG. 5 shows a block diagram of an embodiment of a device 500 to detect cardiac events. The device 500 includes a primary cardiac signal sensing circuit 505 to sense a first cardiac signal. The primary cardiac signal sensing circuit 505 includes at least first and second implantable electrodes. The device 510 also includes at least one secondary cardiac signal sensing circuit 510 to sense at least a second cardiac signal. The secondary cardiac signal sensing circuit 510 includes at least a third implantable electrode that is different from the first and second electrode. The third implantable electrode is used to deliver high-energy shock therapy.

The device 500 also includes an arrhythmia detection circuit 515 communicatively coupled to the primary and secondary cardiac signal sensing circuits. The communicative coupling allows the arrhythmia detection circuit 515 to communicate signals with the primary and secondary cardiac signal sensing circuits even though there may be intervening circuitry. In some examples, the arrhythmia detection circuit 515 includes a processor. The processor may include a digital signal processor, application specific integrated circuit (ASIC), microprocessor, or other type of processor, interpreting or executing instructions in software or firmware. The processor may include one or more modules to provide the functions described herein. A module may include software, hardware, firmware or any combination thereof. For example, the module may include instructions in software executing on or interpreted by the processor. Multiple functions may be performed by one or more modules.

The arrhythmia detection circuit 515 is configured to detect tachyarrhythmia using the primary sensing circuit 505, determine correspondence between events sensed with the primary sensing circuit 505 and events sensed with the secondary sensing circuit 510, and deem whether a detected rhythm is indicative of noise or is indicative of an arrhythmia according to the determined correspondence.

To detect a tachyarrhythmia, the arrhythmia detection circuit 515 may use cardiac depolarizations sensed with the primary sensing circuit 505. Examples of the primary sensing circuit 505 include one or more sensing circuits that sense right or left ventricular depolarizations, such as are typically used in devices to treat bradycardia through pacing therapy and in devices to treat congestive heart failure through resynchronization therapy.

Tachyarrhythmia, such as VT, can be detected by comparing sensed P-waves (atrial depolarizations) and R-waves (ventricular depolarizations). A sudden high ventricular rate with dissociation between P-waves and R-waves may indicate VT. A description of systems and methods that detect tachycardia using rate channels is found in Gilkerson, et al., U.S. Pat. No. 6,522,925, "System and Method for Detection Enhancement Programming," filed May 13, 2000, which is incorporated herein by reference in its entirety.

During normal cardiac events there will be a tight association (e.g., a one-to-one association) between the primary and secondary sensing circuits. During true tachyarrhythmia events (e.g., VF and VT) there will generally still be a tight association of events between the primary and secondary sensing circuits. The association may not remain one-to-one, but events sensed on each of the sensing circuits will be changing in the same way (e.g., increasing). In the presence of noise, the events sensed by each circuit will have lower association or lower correspondence. As discussed previously, this change in association may be because the secondary sensing circuit 510 is less susceptible to the type of noise present due to the difference in electrode arrangement or the difference in signal filtering between the two sensing circuits.

In some examples, to determine correspondence between events sensed with the primary sensing circuit 505 and events sensed with the secondary sensing circuit 510, the arrhythmia detection circuit 515 monitors the delay between events sensed with the primary sensing circuit 505 and events sensed with the secondary sensing circuit 510. The arrhythmia detection circuit 515 measures the delay and calculates variability (e.g., by determining variance) of the delay. The arrhythmia detection circuit 515 deems that the detected rhythm, which is suspected as being a possible tachyarrhythmia, is indicative of noise when the calculated delay variability exceeds a threshold variability value. In some examples, the arrhythmia detection circuit 515 calculates a moving average of the measure of variability and deems that the detected rhythm is indicative of noise when the calculated moving average of the variability exceeds the threshold variability value.

In some examples, to determine the correspondence, the arrhythmia detection circuit 515 determines a number of events sensed with the primary sensing circuit 505 and a number of events sensed with the secondary sensing circuit 510. If the detected rhythm is noise instead of tachyarrhythmia, there will be many more events on the noisy channel than on the other channel. The arrhythmia detection circuit 515 deems that the detected rhythm is indicative of noise when the number of events sensed with the primary sensing circuit 505 during a period of time exceeds the number of events sensed with the secondary sensing circuit 510 during the same time period by a threshold value.

In certain examples, the arrhythmia detection circuit 515 calculates the ratio of the number of events sensed with the primary sensing circuit 505 to the number of events sensed with the secondary sensing circuit 510 during the time period. The arrhythmia detection circuit 515 deems that the detected rhythm is indicative of noise when the calculated ratio exceeds a threshold ratio value.

Some types of noise may affect all of the sensing circuits similarly. For example, electromagnetic interference (EMI) may simultaneously be picked up by an atrial rate channel, a ventricular rate channel, and a shock channel. Therefore, the methods described herein may detect some types of noise (e.g., DMPs) better than other types (e.g., EMI).

Noise due to lead failure typically results in high amplitude artifact signals being sensed by intracardiac sensing circuits and by shock channels. In some examples, the arrhythmia detection circuit 515 monitors the number of events sensed by the secondary sensing circuit 510 (e.g., when the circuit is a shock channel) as well as monitoring the correspondence between the two sensing circuits. The arrhythmia detection circuit 515 deems that the detected rhythm is EMI noise or lead fracture noise when the correspondence determination indicates noise and the number of events sensed with the secondary sensing circuit 510 exceeds a threshold number of events. The arrhythmia detection circuit 515 deems that the detected rhythm is an arrhythmia when the correspondence determination indicates arrhythmia and the number of events sensed with the secondary sensing circuit 510 is less than the threshold.

In some examples, to determine correspondence between events sensed with the primary sensing circuit 505 and events sensed with the secondary sensing circuit 510, the arrhythmia detection circuit 515 compares the complexity of the signals sensed by the primary and secondary sensing circuits. For most cardiac events (in contrast to noise) the signal complexity or signal regularity should be tightly co-variant. If the detected rhythm is sensed noise, the co-variation will no longer hold.

In some examples, the arrhythmia detection circuit 515 determines a measure of complexity of morphology of the first cardiac signal sensed with the primary sensing circuit 505 and a measure of complexity of morphology of the second cardiac signal sensed with the secondary sensing circuit 510. The arrhythmia detection circuit 515 deems that the detected rhythm is indicative of noise when the measure of complexity of the first cardiac signal differs from the measure of complexity of the second cardiac signal by more than a threshold value.

In certain examples, the measure of complexity of the morphology of a cardiac signal includes a measure of similarity. The arrhythmia detection circuit 515 calculates a measure of similarity between the first and second cardiac signals and deems that the detected rhythm is indicative of an arrhythmia when the measure of similarity satisfies a similarity measure threshold value. The measure of similarity may include one or more of a cross-covariance of the first and second cardiac signals, a cross-correlation of the first and second cardiac signals, and a coherence of the first and second cardiac signals.

In some examples, the measure of complexity of morphology includes a measure of cross entropy between the sensed first and second cardiac signals. The arrhythmia detection circuit 515 calculates a cross entropy between the first and secondary cardiac signals, and deems that the detected rhythm is indicative of an arrhythmia when the calculated cross-entropy satisfies a threshold cross-entropy value.

In certain examples, the measure of complexity of morphology can be used together with monitoring the number of events sensed with the secondary sensing circuit to discern whether the noise is EMI or is noise due to lead failure. The arrhythmia detection circuit 515 that the detected rhythm is indicative of noise when the measure of complexity of the first cardiac signal differs from the measure of complexity of the second cardiac signal by more than a threshold value, and the number of events detected with the secondary sensing circuit exceeds a threshold value.

In some examples, the device 500 includes a first switching circuit 520 or switch network. The arrhythmia detection circuit 515 is able to change the arrangement of electrodes and sensing circuits using the switching circuit 520. In certain examples, the switching circuit 520 switches one or more electrodes from the primary sensing circuit 505 to the secondary sensing circuit 510. In certain examples, the switching circuit 520 switches one or more electrodes from the secondary sensing circuit 510 to the primary sensing circuit 505.

When detecting a rhythm that may be tachyarrhythmia, the arrhythmia detection circuit 515 determines one or both of a rate of events sensed with the primary sensing circuit 505 and a rate of events sensed with the secondary sensing circuit 510. The arrhythmia detection circuit 515 then switches one or both of one or more electrodes from the primary sensing circuit 505 to the secondary sensing circuit 510, and one or more electrodes from the secondary sensing circuit 510 to the primary sensing circuit 505. The arrhythmia detection circuit 515 determines the rate of events sensed when the electrode or electrodes are switched, and deems that the detected rhythm is indicative of noise when the determined rate of events changes by more than a threshold rate value after the electrodes are switched. For example, if a high rate of events is detected with the primary sensing circuit 505, and the high rate is then present on the secondary sensing circuit 510 when the sensing electrodes are switched, the rhythm is deemed to be noise.

In some examples, the device 500 includes a second switching circuit 535. The second switching circuit 535 may be in addition to the first switching circuit 520 or the device 500 may only include one of the switching circuits. The arrhythmia detection circuit 515 is able to switch one or more of a filter circuit 525 included in the primary sensing circuit 505 to the secondary sensing circuit 510 and a filter circuit 530 included in the secondary sensing circuit 510 to the primary sensing circuit 505. In certain examples, the first filter circuit 525 includes a frequency bandwidth of about 20.8 Hz-171 Hz. In certain examples, the second filter circuit includes a frequency bandwidth of about 2.2 Hz-80.3 Hz.

When detecting a rhythm that may be tachyarrhythmia, the arrhythmia detection circuit 515, determines one or both of a rate of events sensed with the primary sensing circuit 505 and a rate of events sensed with the secondary sensing circuit 510. The arrhythmia detection circuit 515 then switches one or both of the first filter circuit 525 from the primary sensing circuit 505 to the secondary sensing circuit 510, and the second filter circuit 530 from the secondary sensing circuit 510 to the primary sensing circuit 505.

The arrhythmia detection circuit 515 determines the rate of events sensed when the filter circuit or circuits are switched, and deems that the detected rhythm is indicative of noise when the determined rate of depolarization events changes by more than a threshold rate value after the filter circuit is switched.

According to some examples, the device 500 includes a therapy circuit 540 communicatively coupled to the electrodes of the primary and secondary sensing circuits. The therapy circuit 540 delivers high-energy shock cardioversion therapy or defibrillation therapy using at least one implantable electrode of the secondary sensing circuit 510. In some examples, the therapy circuit 540 optionally delivers ATP therapy.

The device further includes a tachyarrhythmia detection circuit 545 communicatively coupled to the primary and secondary sensing circuits. When the arrhythmia detection circuit 515 deems that the detected rhythm is an arrhythmia instead of noise, the tachyarrhythmia detection circuit 545 determines whether the arrhythmia is a valid tachyarrhythmia (e.g., VF or VT). The tachyarrhythmia detection circuit 545 initiates delivery of a therapy to the heart using the therapy circuit 540 when the tachyarrhythmia is determined to be valid. In some examples, the tachyarrhythmia detection circuit 545 first initiates ATP to convert the detected arrhythmia before resorting to high-energy shock therapy. In some examples, the tachyarrhythmia detection circuit 545 discriminates supraventricular tachycardia (SVT) from VF or VT. In certain examples, the tachyarrhythmia detection circuit 545 initiates ATP upon detecting SVT.

Correctly determining whether a detected possible tachyarrhythmia is noise or is indeed an arrhythmia reduces the number of inappropriate shocks given to the patient, thereby reducing patient discomfort and extending the battery life of the IMD. In some examples, once a detected rhythm is determined to be noise, the arrhythmia detection circuit 515 may generate an alert for the clinician. Based on the nature of the sensed noise, the alert may indicate whether the noise is more likely to be EMI, lead failure, or DMPs. The alert may include a recommendation to check the integrity of the leads or to change a programmable setting to lower sensing sensitivity of one or both of the primary sensing circuit 505 and the secondary sensing circuit 510. In some examples, the device 500 includes a communication circuit to communicate wirelessly with an external device, and the alert is communicated to the external device.

Additional Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a primary cardiac signal sensing circuit configured to sense at least a first cardiac signal, the primary cardiac signal sensing circuit including or configured to be coupled to at least first and second implantable electrodes;
   at least one secondary cardiac signal sensing circuit configured to sense at least a second cardiac signal, the secondary cardiac signal sensing circuit including or configured to be coupled to at least a third implantable electrode, different from the first and second electrode, configured to deliver high-energy shock therapy; and
   an arrhythmia detection circuit communicatively coupled to the primary and secondary cardiac signal sensing circuits, wherein the arrhythmia detection circuit is configured to:
      detect an episode of tachyarrhythmia using the primary sensing circuit;
      determine a measure of one-to-one correspondence of one or more depolarization events sensed with the primary sensing circuit to one or more depolarization events sensed with the secondary sensing circuit during the detected episode of tachyarrhythmia; and
      generate an indication of whether a detected rhythm is indicative of noise or is indicative of tachyarrhythmia according to the determined measure of correspondence.

2. The apparatus of claim 1, wherein the arrhythmia detection circuit is configured to:
   calculate variability of a delay between a depolarization event sensed with the primary sensing circuit and depolarization event sensed with the secondary sensing circuit; and
   deem that the detected rhythm is indicative of noise when the calculated delay variability exceeds a threshold variability value.

3. The apparatus of claim 2, wherein the arrhythmia detection circuit is configured to:
   calculate a moving average of the variability; and
   deem that the detected rhythm is indicative of noise when the calculated moving average of the variability exceeds the threshold variability value.

4. The apparatus of claim 1, wherein the arrhythmia detection circuit is configured to:
   determine a number of events sensed with the primary sensing circuit and a number of events sensed with the secondary sensing circuit; and
   deem that the detected rhythm is indicative of noise when the number of events sensed with the primary sensing circuit during a period of time exceeds the number of events sensed with the secondary sensing circuit during the same time period by a threshold value.

5. The apparatus of claim 4, wherein the arrhythmia detection circuit is configured to:
calculate a ratio of the number of events sensed with the primary sensing circuit to the number of events sensed with the secondary sensing circuit during the time period; and
deem that the detected rhythm is indicative of noise when the calculated ratio exceeds a threshold ratio value.

6. The apparatus of claim 1, wherein the arrhythmia detection circuit is configured to:
determine a measure of complexity of a morphology of the first cardiac signal and a measure of complexity of a morphology of the second cardiac signal; and
deem that the detected rhythm is indicative of noise when the measure of complexity of the first cardiac signal differs from the measure of complexity of the second cardiac signal by more than a threshold value.

7. The apparatus of claim 1, wherein the arrhythmia detection circuit is configured to:
calculate a measure of similarity between the first and second cardiac signals, wherein the measure of similarity includes at least one of a cross-covariance of the first and second cardiac signals, a cross-correlation of the first and second cardiac signals, and a coherence of the first and second cardiac signals; and
deem that the detected rhythm is indicative of an arrhythmia when the measure of similarity satisfies a similarity measure threshold value.

8. The apparatus of claim 1, including:
at least one of a first filter circuit included in the primary sensing circuit or a second filter circuit included in the secondary sensing circuit; and
a switching circuit communicatively coupled to the primary sensing circuit, the secondary sensing circuit, and the arrhythmia detection circuit, wherein the switching circuit is configured to switch at least one of the first filter circuit to the secondary sensing circuit or the second filter circuit to the primary sensing circuit; and
wherein, when detecting the rhythm, the arrhythmia detection circuit is configured to:
determine a rate of events sensed with at least one of the primary sensing circuit and the secondary sensing circuit;
switch at least one of the first filter circuit included with the primary sensing circuit to the secondary sensing circuit, and the second filter circuit included with the secondary sensing circuit to the primary sensing circuit;
determine a rate of events sensed with the sensing circuit when the filter circuit is switched; and
deem that the detected rhythm is indicative of noise when the determined rate of depolarization events changes by more than a threshold rate value after the filter circuit is switched.

9. The apparatus of claim 1, including a switching circuit communicatively coupled to the primary sensing circuit, secondary sensing circuit, and the arrhythmia detection circuit, wherein the switching circuit is configured to switch at least one of the electrodes of the primary sensing circuit to the secondary sensing circuit and the electrodes of the secondary sensing circuit to the primary sensing circuit, and
wherein, when detecting the rhythm, the arrhythmia detection circuit is configured to:
determine a rate of events sensed with at least one of the primary sensing circuit and the secondary sensing circuit;
switch the electrodes of at least one of the primary sensing circuit to the secondary sensing circuit and the secondary sensing circuit to the primary sensing circuit;
determine a rate of events sensed with the sensing circuit when the electrodes are switched, and
deem that the detected rhythm is indicative of noise when the determined rate of events changes by more than a threshold rate value after the electrodes are switched.

10. The apparatus of claim 1, including:
a therapy circuit communicatively coupled to the electrodes of the primary and secondary sensing circuits;
a tachyarrhythmia detection circuit, communicatively coupled to the primary and secondary sensing circuits, configured to determine whether a detected rhythm deemed to be an arrhythmia instead of noise is a valid tachyarrhythmia, and
wherein the tachyarrhythmia detection circuit is configured to initiate delivery of a therapy to the heart using the therapy circuit when the tachyarrhythmia is determined to be valid.

11. A method comprising:
sensing a first cardiac signal using a primary sensing circuit, wherein the primary sensing circuit includes or is configured to be coupled to a first and a second implantable electrode;
sensing a second cardiac signal using at least one secondary sensing circuit, the secondary sensing circuit including or configured to be coupled to at least a third implantable electrode, different from the first and second electrodes, configured to deliver high-energy shock therapy;
detecting an episode of tachyarrhythmia using the primary sensing circuit;
determining a measure of one-to-one correspondence of one or more depolarization events in the first cardiac signal sensed with the primary sensing circuit to one or more depolarization events in the second cardiac signal sensed with the secondary sensing circuit during the detected episode of tachyarrhythmia; and
generating an indication of whether the detected rhythm is indicative of noise or is indicative of tachyarrhythmia according to the determined measure of correspondence.

12. The method of claim 11,
wherein determining correspondence between events includes calculating variability of a delay between an event sensed with the primary sensing circuit and an event sensed with the secondary sensing circuit, and
wherein deeming whether the detected rhythm is indicative of noise or of an arrhythmia includes deeming that depolarization events sensed with the primary sensing circuit are indicative of noise when the calculated delay variability exceeds a threshold variability value.

13. The method of claim 12,
wherein calculating variability of the delay includes calculating a moving average of the variability, and
wherein deeming whether the detected rhythm is indicative of noise includes deeming that events sensed with the primary sensing circuit are indicative of noise when the calculated delay variability average exceeds the threshold variability value.

14. The method of claim 11,
wherein determining correspondence between events includes determining a number of events sensed with the primary sensing circuit during a period of time and a number of events sensed with the secondary sensing circuit during the same time period, and wherein deeming whether the detected rhythm is indicative of noise or of an arrhythmia includes deeming that the detected rhythm is indicative of noise when the number of events sensed during the time period with the primary sensing circuit exceeds the number of events sensed with the secondary sensing circuit during the time period by a threshold value.

15. The method of claim 14, including:

calculating a ratio of the number of events sensed with the primary sensing circuit during the time period to the number of events sensed with the secondary sensing circuit during the time period, and wherein deeming whether the detected rhythm is indicative of noise or an arrhythmia includes deeming that the detected rhythm is indicative of noise when the ratio exceeds a threshold ratio value.

16. The method of claim 11, wherein determining correspondence between events sensed in the primary sensing circuit and events sensed in the secondary sensing circuit includes determining a measure of complexity of a morphology of the first cardiac signal and a measure of complexity of a morphology of the second cardiac signal, and wherein deeming whether the detected rhythm is indicative of noise or an arrhythmia includes deeming that the detected rhythm is indicative of noise when the measure of complexity of the first cardiac signal differs from the measure of complexity of the second cardiac signal by more than a threshold value.

17. The method of claim 11, wherein determining correspondence between events sensed with the primary sensing circuit and events sensed with the secondary sensing circuit includes determining a measure of similarity between the first and second cardiac signals, wherein the measure of similarity includes at least one of a cross-covariance of the first and second cardiac signals, a cross-correlation of the first and second cardiac signals, and a coherence of the first and second cardiac signals, and wherein deeming whether the detected rhythm is indicative of noise or an arrhythmia includes deeming that the detected rhythm is indicative of arrhythmia when the measure of similarity satisfies a similarity measure threshold value.

18. The method of claim 11, wherein determining correspondence between events sensed with the primary sensing circuit and events sensed with the secondary sensing circuit includes:

using a first filter circuit included in the primary sensing circuit to filter the first cardiac signal and a second filter circuit included in the secondary sensing circuit to filter the second cardiac signal;

determining a rate of events with at least one of the primary sensing circuit and the secondary sensing circuit;

switching at least one of the first filter circuit to the secondary sensing switched or the second filter circuit to the primary sensing circuit;

determining a rate of events sensed with the sensing circuit when the filter circuit is switched; and wherein deeming whether the detected rhythm is indicative of noise or an arrhythmia includes deeming that the detected rhythm is indicative of noise when the determined rate of events changes by more than a threshold rate value after the filter circuit is switched.

19. The method of claim 11, wherein determining correspondence between events sensed with the primary sensing circuit and events sensed with the secondary sensing circuit includes:

determining a rate of events sensed with at least one of the primary sensing circuit and the secondary sensing circuit;

switching the electrodes of at least one of the primary sensing circuit to the secondary sensing circuit and the secondary sensing circuit to the primary sensing circuit;

determining a rate of events sensed with the sensing circuit when the electrodes are switched, and wherein deeming whether the detected rhythm is indicative of noise or an arrhythmia includes deeming that the detected rhythm is indicative of noise when the determined rate of events changes by more than a threshold rate value after the electrodes are switched.

20. The method of claim 11, including:

determining whether the detected rhythm is a valid tachyarrhythmia when the detected rhythm is deemed to be an arrhythmia; and delivering at least one of anti-tachycardia pacing and high-energy shock therapy using at least one implantable electrode when the detected rhythm is deemed to be a valid tachyarrhythmia.

* * * * *